(12) United States Patent
Pinkel et al.

(10) Patent No.: US 6,417,506 B1
(45) Date of Patent: Jul. 9, 2002

(54) HIGH DENSITY ARRAY FABRICATION AND READOUT METHOD FOR A FIBER OPTIC BIOSENSOR

(75) Inventors: Daniel Pinkel, Walnut Creek; Joe Gray, San Francisco; Donna G. Albertson, Lafayette, all of CA (US)

(73) Assignees: The Regents of the University of California, Oakland, CA (US); Medical Research Council, London (GB)

( * ) Notice: Subject to any disclaimer, the term of this patent is extended or adjusted under 35 U.S.C. 154(b) by 0 days.

(21) Appl. No.: 09/642,243

(22) Filed: Aug. 17, 2000

Related U.S. Application Data

(62) Division of application No. 08/899,000, filed on Jul. 24, 1997, now Pat. No. 6,146,593, which is a division of application No. 08/448,043, filed on May 23, 1995, now Pat. No. 5,690,894.

(51) Int. Cl.[7] .............................................. C25D 13/00
(52) U.S. Cl. .................. 250/216; 250/227.11; 204/603; 600/473
(58) Field of Search ........................... 250/216, 227.11, 250/227.2, 227.24, 227.28, 458.1, 461.1, 461.2, 492.1, 492.2; 356/302, 317; 385/12, 30, 33, 34, 35; 204/603, 605, 612; 600/407, 473, 476

(56) References Cited

U.S. PATENT DOCUMENTS

| 4,447,546 A | 5/1984 | Hirschfeld ................... 436/527 |
| 4,582,809 A | 4/1986 | Block et al. ................. 436/527 |

(List continued on next page.)

FOREIGN PATENT DOCUMENTS

| WO | WO 93/18186 | 9/1993 |
| WO | WO 95/35505 | 12/1995 |

OTHER PUBLICATIONS

Dalbe, B. and Peguy, A., "Method to Determine the Degree of Polymerization of Cellulose in the Solvent System: MMNO/$H_2O$/DMSO," *Cellulose Chemical Technology* 24:327–331 (1990).

(List continued on next page.)

*Primary Examiner*—Stephone Allen
(74) *Attorney, Agent, or Firm*—Emily M. Haliday; Quine Intellectual Property Law Group, P.C.

(57) ABSTRACT

The invention relates to the fabrication and use of biosensors comprising a plurality of optical fibers each fiber having attached to its "sensor end" biological "binding partners" (molecules that specifically bind other molecules to form a binding complex such as antibody-antigen, lectin-carbohydrate, nucleic acid-nucleic acid, biotin-avidin, etc.). The biosensor preferably bears two or more different species of biological binding partner. The sensor is fabricated by providing a plurality of groups of optical fibers. Each group is treated as a batch to attach a different species of biological binding partner to the sensor ends of the fibers comprising that bundle. Each fiber, or group of fibers within a bundle, may be uniquely identified so that the fibers, or group of fibers, when later combined in an array of different fibers, can be discretely addressed. Fibers or groups of fibers are then selected and discretely separated from different bundles. The discretely separated fibers are then combined at their sensor ends to produce a high density sensor array of fibers capable of assaying simultaneously the binding of components of a test sample to the various binding partners on the different fibers of the sensor array. The transmission ends of the optical fibers are then discretely addressed to detectors—such as a multiplicity of optical sensors. An optical signal, produced by binding of the binding partner to its substrate to form a binding complex, is conducted through the optical fiber or group of fibers to a detector for each discrete test. By examining the addressed transmission ends of fibers, or groups of fibers, the addressed transmission ends can transmit unique patterns assisting in rapid sample identification by the sensor.

7 Claims, 5 Drawing Sheets

U.S. PATENT DOCUMENTS

| | | | | |
|---|---|---|---|---|
| 4,909,990 | A | | 3/1990 | Block et al. ............. 422/42.11 |
| 5,047,627 | A | | 9/1991 | Yim et al. |
| 5,061,857 | A | | 10/1991 | Thompson et al. ...... 250/458.1 |
| 5,082,630 | A | | 1/1992 | Partin et al. .................. 422/83 |
| 5,135,876 | A | | 8/1992 | Andrade et al. ............ 436/518 |
| 5,166,990 | A | | 11/1992 | Riccitelli et al. ............. 385/12 |
| 5,194,393 | A | | 3/1993 | Hugl et al. ................. 436/525 |
| 5,244,636 | A | | 9/1993 | Walt et al. ............... 422/82.07 |
| 5,250,264 | A | | 10/1993 | Walt et al. ............... 422/82.08 |
| 5,260,029 | A | | 11/1993 | Hosoi et al. ............ 422/82.08 |
| 5,304,492 | A | | 4/1994 | Klinkhammer ............. 436/52 |
| 5,344,784 | A | | 9/1994 | Attridge ..................... 436/518 |
| H1398 | H | | 1/1995 | Campbell ...................... 435/6 |
| 5,449,625 | A | | 9/1995 | Kobayashi et al. ......... 436/518 |
| 5,494,798 | A | | 2/1996 | Gerdt et al. .................... 435/6 |
| 5,516,409 | A | * | 5/1996 | Kambara .................... 204/603 |
| 5,690,894 | A | | 11/1997 | Pinkel et al. ............. 422/68.1 |
| 5,750,337 | A | | 5/1998 | Squirrell ........................ 435/6 |
| 5,777,342 | A | * | 7/1998 | Baer ....................... 250/492.2 |
| 5,800,992 | A | | 9/1998 | Fodor et al. .................... 435/6 |
| 5,830,645 | A | | 11/1998 | Pinkel et al. ................. 435/6 |
| 5,840,484 | A | | 11/1998 | Seilhamer et al. ............ 435/6 |
| 6,104,945 | A | * | 8/2000 | Modell et al. .............. 600/473 |
| 6,192,168 | B1 | * | 2/2001 | Feldstein et al. ............. 385/12 |

OTHER PUBLICATIONS

Hartmann, A. et al., "One–step immobilization of immunoglobin G and potential of the method for application in immunosensors," *Sensors and Actuators* 28:2:143–149 (Aug. 1, 1995).

Hartmann, A. et al., "Cellulose as a New Matrix For One–Step Immobilized Antibodies and Application in High Specific Immunosensors,"*Proceedings of the International Solid–State Sensors and Actuators Conference—Transducers '95*, 2:505–508 (Jun. 25–29, 1995).

Anderson et al., "Fiber Optic Based Biosensor: Signal Enhancement in a Production Model" *Proceedings SPIE—The Intl. Soc. For Optical Engineering* 1648:39–43 (Jan. 23–24, 1992).

Barnard et al., *Nature* 353–338–340 (Sep. 1991).

Blum et al., *Anal. Chim Acta* 21:5:717–726 (1988).

Blum et al., *Anal. Chim Acta* 226:2:331–336 (1989).

Graham et al., "Gene Probe Assays on a Fibre–optic Evanescent Wave Biosensor" *Biosens. Bioelectron.* 7:487–493 (1992).

Hlavay et al., *Biosensors and Bioelectronics* 9:3:189–195 (1994).

Kallioniemi et al., "Comparative Genomic Hybridization For Molecular Cytogenetic Analysis of Solid Tumors" *Science* 258:818–821 (1992).

Krug et al., *Anal. Chim. Acta* 256:2:263–268 (1992).

Lipson et al, *IEEE Trans. On Biomed. Engineering* 39:9:886–892 (Sep. 1992).

Marx et al., *J. Intelligent Material System Systems and Structures* 5:4:447–454 (1994).

McCurley, *Biosensors and Bioelectronics* 9:527–533 (1994).

Myrick et al., "Fluorescence Microstructure Using a Laser/Fiber Optic Profiler" *Proceedings of SPIE—The Intl. Soc. For Optical Engineering* 1302:336–345 (Apr. 16–18, 1990).

Piunno et al., "Fiber Optic Biosensor for Fluorimetric Detection of DNA Hybridization" *Anal. Chim. Acta* 288:205–214 (1994).

Piunno et al., *Anal. Chem.* 67:2635–2643 (Aug. 1995).

Steinitz et al., "An Improved Method to Create Nitrocellulose Particles Suitable for the Immobilization of Antigen and Antibody" *J. Immunol. Meth.* 187:1:171–177 (1995).

Thomas, "Hybridization of Denatured RNA and Small DNA Fragments Transferred to Nitrocellulose" *Proc. Natl. Acad. Sci.* 77:9:5201–5205 (1980).

* cited by examiner

HIGH DENSITY ARRAY FABRICATION AND READOUT METHOD FOR A FIBER OPTIC BIOSENSOR

CROSS-REFERENCE TO RELATED APPLICATIONS

This is a Divisional of U.S. Ser. No. 08/899,000, filed on Jul. 24, 1997, now U.S. Pat. No. 6,146,593 which is a Divisional of U.S. Ser. No. 08/448,043, filed on May 23, 1995, now U.S. Pat. No. 5,690,894 which is incorporated herein by reference for all purposes.

This invention was made with the Government support under Grant No. CA 45919, awarded by the National Institute of Health and under Grant No. DE-AC03-76SF0098, awarded by the Department of Energy. The Government has certain rights in this invention.

FIELD OF THE INVENTION

This invention relates to the fabrication and use of biosensors comprising biological "binding partners" (molecules that specifically bind other molecules to form a binding complex such as antibody-antigen, lectin-carbohydrate, nucleic acid-nucleic acid, biotin-avidin, etc.) linked to optical fibers. Specifically, batches of optical fibers are mass processed with the same species of binding partner, singulated from their particular batch, regrouped with like optical fibers from other batches having other species of binding partners. Upon regrouping of the optical fibers, high density arrays are formed which can simultaneously interrogate samples for a multiplicity of analytes for sample identification and processing.

BACKGROUND OF THE INVENTION

Biosensors are sensors that detect chemical species with high selectivity on the basis of molecular recognition rather than the physical properties of analytes. See, e.g., *Advances in Biosensors*, A. P. F. Turner, Ed. JAI Press, London, (1991). Many types of biosensing devices have been developed in recent years, including enzyme electrodes, optical immunosensors, ligand-receptor amperometers, and evanescent-wave probes. Updike and Hicks, *Nature*, 214: 986 (1967), Abdel-Latif et al., *Anal. Lett.*, 21: 943 (111988); Giaever, *J. Immunol.*, 110: 1424 (1973); Sugao et al. *Anal. Chem.*, 65: 363 (1993), Rogers et al. *Anal. Biochem.*, 182: 353 (1989).

Biosensors comprising a biological "binding molecule" attached to an optical fiber are well known in the prior art, most typically as evanescent wave detectors (see, for example, U.S. Pat. No. 4,447,546 to Hirschfeld and U.S. Pat. Nos. 4,582,809 and 4,909,990 to Block et al.). In order to maximize sensitivity and selectivity such biosensors typically utilize a single species of biological binding molecule affixed to the face of the sensor.

Such "single-species" biosensors are limited in that they have no inherent means to correct or calibrate for non-specific binding. Thus, they must be calibrated against an external standard. In addition, they are limited to the detection of a single analyte.

Biosensors comprising two or more species of biological binding partners overcome these limitations. A "multi-species" biosensor in principle permits simultaneous detection of as many different types of analytes as there are species of biological binding partner incorporated into the sensor. In addition, comparison of the amounts of a single analyte binding to multiple species of binding partner provides a measure of non-specific binding and thus acts as an intrinsic control for measurement variability introduced by non-specific binding.

In addition, the inclusion of fibers bearing biological binding partners specific for various analytes known to create a background signal in a particular assay provides a means for simultaneously measuring and substracting out the background signal. The provision of a multiplicity of fibers bearing different species of binding partner allows the detection of a multiplicity of moieties contributing to a background, or other, signal and the dissecting out of the contribution of each moiety to that signal.

To be most useful, a multi-species biosensor requires that the sensor provide a separate signal characterizing binding of analytes to each of the various species of binding partner comprising the probe. Thus each species of binding partner must be individually "addressed".

In addition, a "sensor face" (the surface bearing the biological binding partners) that has a relatively small surface area will facilitate measurement of small sample volumes as less sample material will be required to fully immerse the sensor face. A small surface area detector will also prove advantageous for use in in vitro measurements. Preparation of a detector bearing a large number of different biological binding partners that occupies a small area may be viewed as the preparation of a high density array of biological binding partners.

The creation of high density arrays of biological binding partners where each species of binding partner is uniquely addressed presents formidable fabrication problems. One of the most successful approaches, to date, is the large scale photolithographic solid phase synthesis pioneered by Affymax Inc. (see, e.g., Fodor et al. *Science* 251: 767–773 (1991) and U.S. Pat. No. 5,143,854). In this approach arrays of peptides or nucleic acids are chemically synthesized on a solid support. Different molecules are simultaneously synthesized at different predetermined locations on the substrate by the use of a photolithographic process that selectively removes photolabile protecting groups on the growing molecules in particular selected locations of the substrate. The resulting array of molecules is "spatially addressed". In other words the identity of each biological molecule is determined by its location on the substrate.

The photolithographic approach, however, is limited to molecules that can be chemically synthesized. Thus, it is typically restricted to peptides shorter than about 50 amino acids and nucleic acids shorter than about 150 base pairs. In addition, the photolithographic approach typically produces such arrays on a planar substrate (e.g. a glass slide) and provides no intrinsic mechanism by which a signal produced by the binding of a particular biological binding partner may be transmitted.

U.S. Pat. No. 5,250,264 to Walt et al. discloses a sensor comprising a fiber optic array using a "plurality of different dyes immobilized at individual spatial positions on the surface of the sensor." Each dye is capable of responding to a different analyte (e.g., pH, $O_2$, $CO_2$, etc.) and the sensor as a whole is capable of providing simultaneous measurements of multiple analytes.

Although the sensor disclosed by Walt et al. is not a biosensor, the reference describes a means of fabricating a sensor bearing a plurality of uniquely addressed "detection moieties". In Walt et al. optical fibers are first assembled to form a bundle. Transmission ends of a fiber or group of fibers of are then specifically illuminated. Each illuminated fiber transmits the light to its respective sensor end where the light "photopolymerizes" a sensor dye mixture causing the dye to bind to the sensor end. This process is repeated with different fibers for different photopolymerized dyes. This repetition continues until a sensor array is constructed.

This approach suffers from the limitations that it requires photopolymerizable sensor dyes and thus is limited in the number of different species per probe by the number of different dye type. In addition, this reference provides no means for attaching uniquely addressed biological molecules (e.g. peptides, nucleic acids, antibodies) to the sensor. Thus Walt et al. provide no means for the fabrication of biosensors.

SUMMARY OF THE INVENTION

The present invention provides a novel means for fabricating biosensors comprising a plurality of biological "binding partners" (molecules that specifically bind other molecules to form a binding complex such as antibody-antigen, lectin-carbohydrate, nucleic acid-nucleic acid, biotin-avidin, etc.) linked to optical fibers. In particular the method provides a means of preparing a high density array of biological binding partners where each species of binding partner is uniquely addressed. In contrast to certain methods in the prior art the biological binding partners utilized in the present invention are not limited to chemically synthesized oligonucleotides or peptides, but rather include nucleic acids, antibodies, proteins, lectins and other binding partners derived from cells, tissues or organisms in their native state or otherwise modified through the methods of recombinant DNA technology.

In particular, the biosensors of the present invention comprise a multiplicity of optical fibers bundled together to form an optical fiber array. The sensor end of each optical fiber or group of optical fibers comprising the optical fiber array bear a particular species of biological binding partner. Optical signals produced by binding of an analyte to a biological binding partner are conducted along the respective optical fibers to a transmission end which may be attached to a detector. Detection of the signal from the fibers corresponding to each species of biological binding partner provides a simultaneous measurement of the binding of a multiplicity of analytes.

The present invention provides a method of fabrication of fiber optic biosensors. The method involves providing a multiplicity of optical fibers which are grouped into a plurality of separate fiber groups or batches. Each fiber has a sensor end and a transmission end and the fibers in each group are oriented so that the sensor ends are commonly aligned. Each group of fibers is then treated to attach a single species of biological binding partner to the sensor ends of the constituent fibers. Alternatively, a multiplicity of species of biological binding partner may be attached to each group as long as the multiplicity of species of biological binding partners attached to one fiber group is different than the multiplicity of species attached to the other fiber groups.

Fibers or groups of fibers are then selected and discretely separated from their respective batches. One or more of the discretely separated fibers from each group are then recombined at their sensor ends with other fibers from other batches to produce an optical fiber array. The sensor ends may be arranged in a substantially planar orientation or may be tiered to form a tiered sensor face. The optical fiber array contains fibers capable of assaying simultaneously the binding of components of a test sample to the various binding partners on the different fibers of optical fiber array.

The batch identity of each fiber is maintained during the bundling process, preferably at or adjacent to the transmission end of the fibers. These transmission ends are then discretely addressed to detectors—such as a multiplicity of optical sensors. The location and spatial array of the transmission ends corresponding to particular biological binding partners are distinct from one another and known.

Thus, the invention provides for the fabrication of a high density array of biological binding partners in which each binding partner is uniquely addressed. An optical signal, produced by binding of the binding partner to its substrate to form a binding complex, is conducted through the optical fiber or group of fibers to a detector for each discrete test. Thus, binding of a molecule to a particular biological binding partner is specifically detectable. By examining the addressed transmission ends of fibers, or groups of fibers, the addressed transmission ends can transmit unique patterns assisting in rapid sample identification of analytes by the sensor.

In one embodiment, the fiber optics might bear nucleic acid binding partners to which nucleic acids in the test sample might hybridize. As used herein, the terms polymer in either single- or double-stranded form, and unless otherwise limited, would encompass known analogs of natural nucleotides that can function in a similar manner as naturally occurring nucleotides.

In one particularly preferred embodiment, the biosensor comprises a plurality of fibers, each fiber including an sensor end and a transmission end, the sensor end of at least one first fiber having attached a first biological binding partner and the sensor end of at least one second fiber having attached a second biological binding partner, a transmission array having first and second positions addressing the transmission ends of the first and second fibers, means for addressing the transmission ends of the first and second fibers to the transmission array, optical interrogation means adjacent the transmission ends for examining the comparative attachment of analytes at the sensor ends of the fibers. The sensor ends of the first and second fibers may be arranged to form a tiered sensor face. The first and second binding partners may be nucleic acids, for example, DNA and cDNA, and the nucleic acids may be mapped to specific regions on one or more human chromosomes. In a particularly preferred embodiment, the target nucleic acids are about 1,000 to 1,000,000 nucleotides in complexity.

Nucleic acid bearing arrays are particularly useful in Comparative Genomic Hybridization (CGH) assays to detect chromosomal abnormalities; in particular increases or decreases in copy number of particular chromosomal regions. In one example of this approach, a first collection of (probe) nucleic acids is labeled with a first label, while a second collection of (probe) nucleic acids is labeled with a second label. A biosensor, as described above, is one in which the biological binding partners are target nucleic acids. (As used herein the term "target nucleic acids" typically refers to nucleic acids attached to the optical fibers comprising the fiber optic array, while "probe nucleic acids" are those nucleic acids free in solution that hybridize with the target nucleic acids.) The ratio of hybridization of the nucleic acids is determined by the ratio of the two (first and second) labels binding to each fiber in the array. Where there are chromosomal deletions or multiplications, differences in the ratio of the signals from the two labels will be detected. Identification of the specific optical fibers in the array giving rise to these ratios will indicate the nucleic acid sequence the probe bears and thus the nucleic acid sequence that is altered.

The target nucleic acids (the nucleic acids attached to the optical fibers) may include DNA and cDNA and may be mapped to specific regions in human chromosomes. In addition, the target nucleic acids are preferably about 1,000 to 1,000,000 nucleotides in complexity. The complexity of the sequence complementary to the target nucleic acid is preferably less than 1% of the total complexity of the sequences in the sample.

The first and second labels are preferably fluorescent labels. In a particularly preferred embodiment, the first probe nucleic acids comprise mRNA or cDNA from a test cell and the second probe nucleic acids comprise mRNA or cDNA from a reference cell. In another preferred embodiment, the first probe nucleic acids are from a test genome and the second probe nucleic acids are from a reference genome. The test genome may comprise nucleic acids from fetal tissue or from a tumor.

According to one aspect of the invention, arrays of optical fibers are disclosed where the interrogating end of each fiber in the array comprises a multiplicity of biological "binding partners." Each binding partner is attached to one or more optical fibers specifically addressed or identified at the transmitting end as being connected to the particular binding partner. With the transmission ends properly addressed and interrogated, measurement occurs.

In one specific embodiment, arrays of optical fibers bearing nucleic acid molecules are disclosed. These optical fibers at their interrogating ends have specific nucleic acids such as nucleic acids having a certain minimum length (e.g. 400 bp), or being derived from particular libraries (e.g. evenly spaced along a particular chromosome or representing a particular gene).

It is an advantage of the disclosed apparatus and process that the constructed array can be tailored to rapid screening of extensive arrays of biological binding partners. Using already identified information, arrays can be assembled which can simultaneously and rapidly survey samples nucleic acid variations across entire genomes. For example, a fiber optic sensor bearing 30,000 target nucleic acids, each containing 100 kb of genomic DNA could give complete coverage of the human genome.

DESCRIPTION OF THE PREFERRED EMBODIMENT

Figure 1:
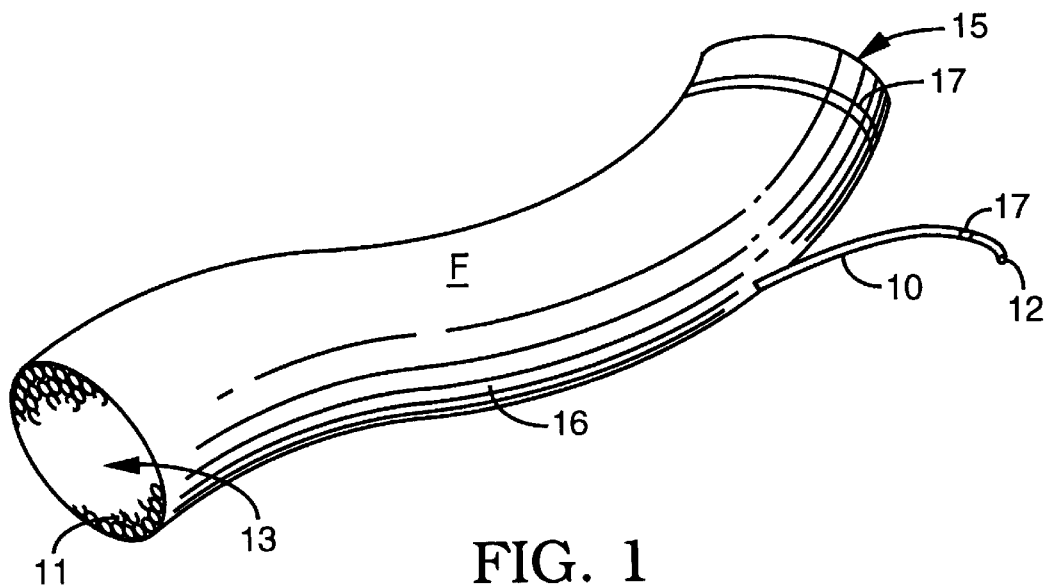
FIG. 1 is a schematic illustration showing a group of fibers with the sensor ends bound together for joint treatment to attach a binding partner and the transmission ends discretely marked to enable the fibers of the illustrated group to be distinguished from fibers of similar groups when subsequent separation of the fibers later occurs from the group.

The present invention is a marked improvement in fiber optic biosensors, methods for fabricating biosensors, and methods for performing qualitative and quantitative measurements of biological molecules using a unique fiber optic biosensor. In particular, the present invention provides for a novel method of construction of a biosensor comprising a high-density array of biological binding partners.

The biosensors of the present invention generally comprise a bundle of coalligned optical fibers. Each individual optical fiber or group of fibers within the biosensor bears a single species of biological binding partner. As used herein biological binding partners are molecules that specifically recognize and bind other molecules thereby forming a binding complex. Typical binding complexes include, but are not limited to, antibody-antigen, lectin-carbohydrate, nucleic acid-nucleic acid, biotin-avidin, receptor-receptor ligand, etc.

The terms "specifically recognize and bind" refers to the binding of a biological binding partner to a particular molecule and to no other molecule to which the biological binding partner is normally exposed. In the case of nucleic acids, specific binding is by hybridization and the terms "specific hybridization" or "specifically hybridizes with" refers to hybridization in which a probe nucleic acid binds substantially to target nucleic acid and does not bind substantially to other nucleic acids present in the biosensor under defined stringency conditions. One of skill will recognize that relaxing the stringency of the hybridizing conditions will allow sequence mismatches to be tolerated. The degree of mismatch tolerated can be controlled by suitable adjustment of the hybridization conditions.

The term "species", as used herein, refers to a biological binding partner capable of specifically binding a particular target molecule. Thus, for example, biological binding partners may both be nucleic acids, but if they have different nucleotide sequences, so that they specifically hybridize to different molecules, they are considered different species. Similarly, two antibodies specific for different epitopes are considered different species.

In a preferred embodiment, the biosensor bears two or more different species of biological binding partner. The use of two or more species of binding partner permits the simultaneous detection of two or more analytes in a test sample with the number of detectable analytes limited only by the number of different biological binding partners present on the biosensor. The biosensor may optionally include additional optical fibers lacking biological binding partners. These additional fibers may bear moieties for the detection of various physical parameters of the test sample, such as temperature or pH, or alternatively may lack any moiety and simply serve as an optical conduit for visualization thereby serving as an endoscope for guiding the insertion of the biosensor probe in various in vivo applications.

A biosensor bearing a plurality biological binding partners permits the simultaneous assay of a multiplicity of analytes in a sample. In addition, the measurement of binding of a single analyte to a number of different species of biological binding partners provides a control for non-specific binding. A comparison of the degree of binding of different analytes in a test sample permits evaluation of the relative increase or decrease of the different analytes. Finally, because of the small cross-sectional area of optical fibers, the bundling together into an optical array a number of optical fibers, each bearing a different biological binding partner, provides an effective mechanism for the fabrication of high density arrays of biological binding partners for suitable for a wide variety of in vivo and in vitro assays.

I. Organization of the Biosensor

The unique fiber optic biosensor of the present invention, its organization, its construction and its component parts are illustrated by FIGS. 1–6 respectively. Each discrete fiber optic biosensor is comprised of a plurality of fiber optic strands 10 disposed coaxially along their lengths to form a single, discrete construction. The biosensor thus comprises an optical fiber array 14, the smallest common repeating unit within which is a single fiber optical strand 10.

Figure 4:
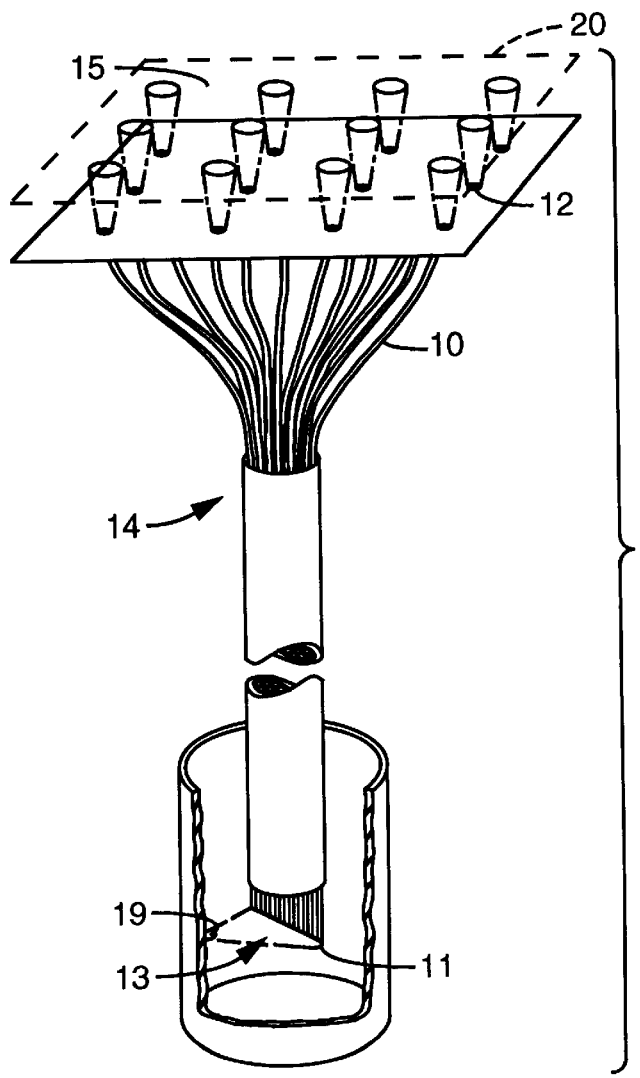
FIG. 4 illustrates an assembled high density array at the sensor and transmitting ends only with disposition of the sensor ends in a tiered disposition for transillumination by interrogating light and the detector ends identified and discretely addressed to a sensor array, the sensor array here illustrated having a corresponding array of condensing lenses for relaying fiber illumination to a detector surface.

A preferred fiber optical biosensor is illustrated by FIG. 4. As seen therein an individual fiber optical strand 10 comprises a single optical fiber having a rod-like shaft and two fiber ends designated a sensor end 11 and a transmission end 12 each of which provides a substantially planar end surface. The optical fiber strand 10 is typically composed of glass or plastic and is a flexible rod able to convey light energy introduced at either of its ends 11, 12. Such optical fibers 10 are conventionally known and commercially available. Alternatively, the user may himself prepare optical fibers in accordance with the conventional practices and techniques reported by the scientific and industrial literature. Accordingly, the optical fiber 10 is deemed to be conventionally known and available as such.

It will be appreciated that FIGS. 1–6 are illustrations in which the features have been purposely magnified and exaggerated beyond their normal scale in order to provide both clarity and visualization of extreme detail. Typically, the conventional optical fiber has a cross section diameter of 5–500 micrometers and is routinely employed in lengths ranging between centimeters (e.g. in the laboratory) to kilometers (e.g. in field telecommunications). Typically, however, when utilized in a biosensor, the optical fibers will preferably range in length from centimeters to about a meter.

Although the optical fiber 10 is illustrated via FIGS. 1–4 as a cylindrical extended rod having substantially circular end surfaces, there is no requirement or demand that this specific configuration be maintained. To the contrary, the optical fiber may be polygonal or asymmetrically shaped along its length, provide special patterns and shapes at the sensor end or transmission end and need not present an end surface that is substantially planar. Nevertheless, in a preferred embodiment, the optical fiber is substantially cylindrical.

Each optical fiber 10 may be individually clad axially along its length. The cladding may be any material which has a lower refractive index and prevents the transmission of light energy photons from the optical fiber 10 to the external environment. The cladding may thus be composed of a variety of different chemical formulations including various glasses, silicones, plastics, cloths, platings and shielding matter of diverse chemical composition and formulation. Methods of cladding including deposition, extrusion, painting and covering are scientifically and industrially available and any of these known processes may be chosen to meet the requirements and convenience of the user.

The user has a variety of choices at his discretion regarding the configuration of the sensor end 11 of the optical fiber 10. As indicated above, the sensor end 11 may present a surface that is substantially planar and smooth. Alternatively the sensor end 11 may provide an end surface which is essentially convex or concave.

It will be appreciated that the range and variety of dimensional and configurational variation of the optical fiber 10 is limited only by the user's ability to subsequently dispose and immobilize a biological binding partner on the intended sensor end 11 of the strand. The use of concave or convex sensor ends 11 will provide greater surface area upon which to immobilize a biological binding partner thereby increasing efficiency (the signal to noise ratio per optical fiber) of the biosensor.

Figure 6A:
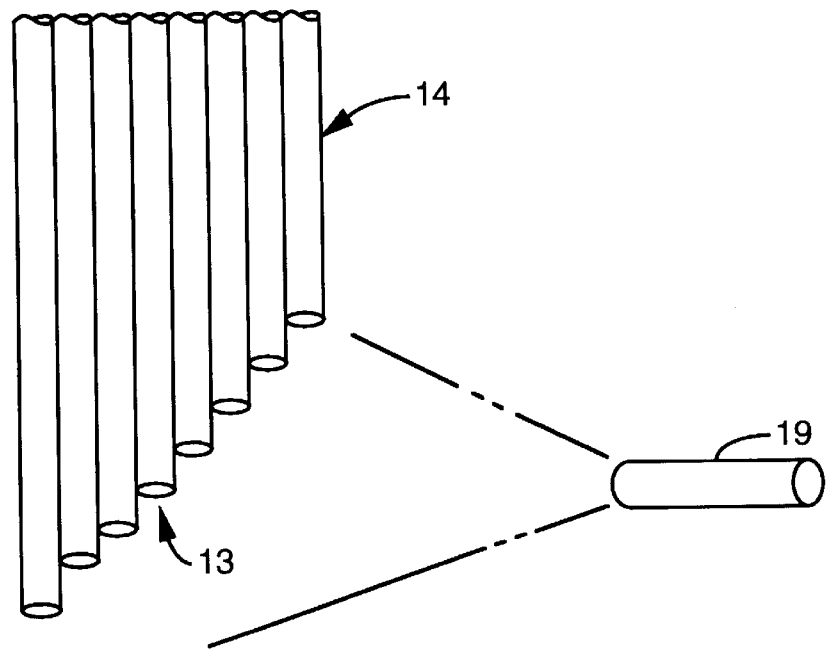
FIGS. 6A and 6B illustrate an expanded detail of the common batch of FIG. 5 being transilluminated at the tiered sampling fibers at the sensor end of the array for the excitation of fluorophores attached to the binding partners without undue direct illumination of the fibers themselves.
Figure 6B:
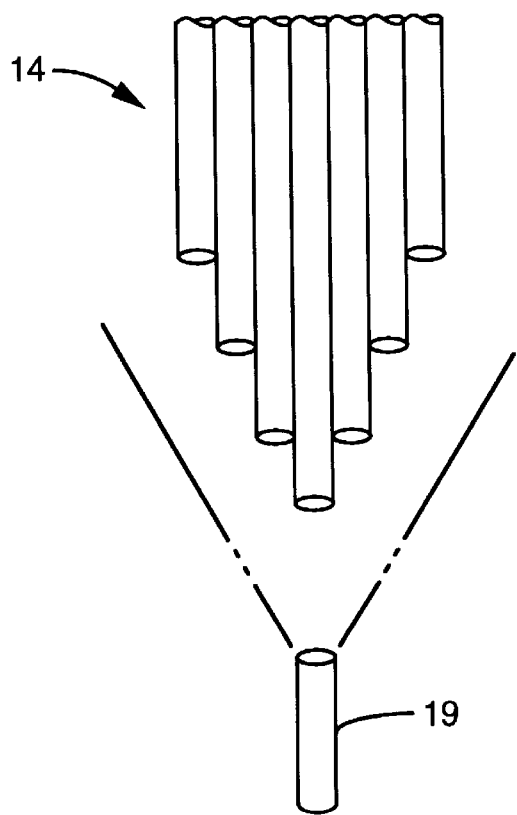

While the single repeating component of the fiber optic biosensor is the individual optical fiber 10, it is the aggregation of a plurality of such fibers to form a discrete optical fiber array 14 that permits the simultaneous detection of a multiplicity of analytes. When the optical fibers are aggregated to form a discrete optical fiber array 14, the coaligned sensor ends 11 of the fibers are aggregated to form a sensor face 13. A typical biosensor is illustrated in FIG. 4 and FIGS. 6A and 6B in which the sensor face 13 appears in exaggerated, highly simplified views without regard to scale. The optical fiber array 14 comprises a unitary rod-like collective body forming a sensor face 13 and a and a transmission face 15.

In practice, it is estimated that there are typically 1000–3000 fiber optical strands in a conventional imaging fiber of 0.5 mm diameter and nearly 1 million strands per square millimeter. The total number of individual fiber optic strands forming the optical fiber array 14 of the present invention will be approximately as great; the total number varying with the cross-sectional diameter of each optical fiber, the pattern of packing of the individual optical fibers in the collective body, and the thickness of cladding material, when employed. It will be appreciated that a 1 square millimeter biosensor, containing nearly 1 million strands in which groups of about 33 optical fibers are each labeled with a different species of biological binding partner will produce a sensor face 13 comprising approximately 30,000 different species of biological binding partner in 1 square millimeter. As explained above, such a sensor could provide nucleic acid biological binding partners covering the entire human genome at 10 megabase intervals.

The sensor face 13 need not be arranged as a planar surface. Rather, the individual optical fibers may be "tiered" so as to protrude from the optical array varying distances. This will maximize the exposure of each optical fiber sensor end 11 both to the sample fluid and to a transilluminating light source 19 as shown in FIGS. 6A and 6B.

In a preferred embodiment, the sensor ends 11 of the optical fibers comprising the optical fiber array 14 will be bundled together in a random or haphazard pattern to form the sensor face 13. Alternatively, the placement of the sensor ends 11 may be highly ordered with the sensor end of each fiber occupying a specific predetermined location in the sensor face 13. As indicated above, the sensor ends 11 of the optical fibers 10 forming the sensor face 13 or the optical fiber array 14 have attached a biological binding partner.

Each optical fiber or group of fibers comprising the optical fiber array 14 may bear a different species of biological binding molecule. Although the use of a single species of biological binding partner per optical fiber or group of fibers is preferred, alternatively, each optical fiber or group of fibers may bear a multiplicity of biological binding partners as long as that multiplicity differs from the biological binding partners or multiplicity of biological binding partners present on other fibers or groups of fibers comprising the optical fiber array 14. The fibers bearing like species of binding partner may be physically grouped together thereby producing distinct regions of the sensor face 13 characterized by the presence of a particular biological binding partner or alternatively the fibers bearing different binding partners may be intermingled, the sensor face 13 presenting a relatively uniform or haphazard or random distribution of species of biological binding partners.

The transmission face 15 of the optical array may present a substantially planar optical array lacking any further attachments. However, in a preferred embodiment, the transmission face 15 will be permanently or removeably attached to a detector 20, as illustrated in FIG. 4. The detector may comprise one or more lenses for focusing and enhancement of an optical signal transmitted along the optical fibers comprising the optical fiber array 14. The detector may additionally comprise a device for transforming the optical signal into a digital or analog electrical signal. Preferred detectors include phototubes (photomultipliers) or charge coupled devices (CCDs). A single photomultiplier or CCD element may be arranged to measure the aggregate signal provided by the entire transmission face 15 of the biosensor. Alternatively, a CCD (or other) camera may be focused at the transmission face of the biosensor to simultaneously read signals from all of the optical fibers while permitting individual evaluation of the signal from each fiber or group of fibers. In another embodiment, multiple CCD elements or phototubes are used to each detect a signal representing binding of a single species of biological binding partner present at the sensor face 13 of the biosensor. Thus the detector is preferably arranged to read the signal from single optical fibers 10 or from groups of optical fibers where all of the optical fibers 10 in a group bear the same species of biological binding partner.

In addition to detecting optical signals from a fiber optic array, the detector 20, may be generally used to amplify and detect optical signals from any array of light sources. Thus, for example, the array of light sources may be an array of fluorescent spots as due to hybridization of fluorescently labeled probes hybridized to arrays of target nucleic acids. Similarly, the array may be of fluorescently labeled antibodies bound to an array of proteins to which the antibodies bind, or conversely fluorescently labeled proteins bound to an array of antibodies.

Figure 7A:
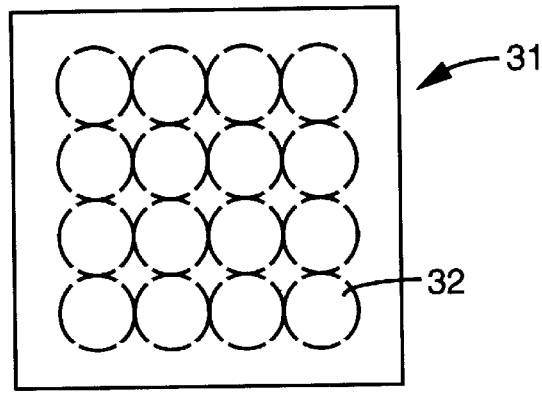
FIGS. 7A and 7B illustrate a detector that may be used in conjunction with an optical fiber array or with any other array of light sources (e.g. an array of hybridized fluorescent probes).
Figure 7B:
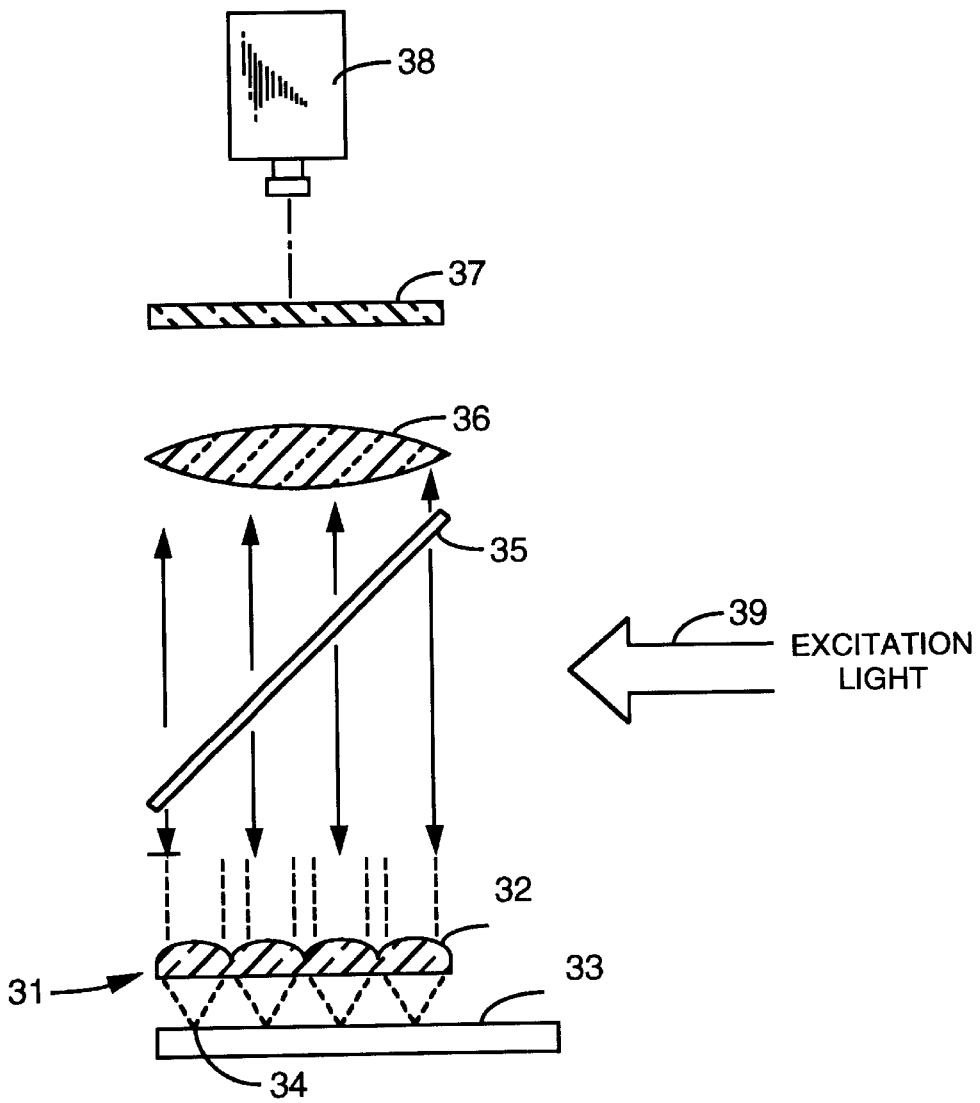

In a preferred embodiment suitable for such applications, illustrated in FIGS. 7A and 7B, the detector 20 may comprise a compound objective lens 31 that consists of an array of single lenses 32. The single lenses are spaced so that each lens is focused on a location 34 in the array where fluorescence is to be measured. The detector may optionally include a beam splitter 35 a second lens 36 an optical filter 37 and a detection device such as a camera 38. The beam splitter is then used to direct an excitation illumination 39 upon the array of light sources. The resulting fluorescence at each spot is then focused through the compound objective lens 31 optionally focused by a second lens, optionally filtered by an optical filter and then detected either visually or by a detection means such as a camera.

The compound objective may be cast, pressed, etched, or ground out of glass, plastic, quartz, or other materials well known as suitable for lens manufacture. The compound lens may be formed as a single piece, or alternatively may be assembled by attaching together simple lenses to form a compound objective.

II. Fabrication of the Biosensor

FIGS. 1–4 illustrate a method of fabrication of a biosensor comprising a plurality of optical fibers bearing biological binding partners. In general the method involves providing a plurality of optical fibers with each fiber having a sensor end and a transmission end with a particular species of biological binding partner attached to the sensor end of each fiber. Fibers with differing binding partners are combined to form an optical fiber array wherein said fibers have commonly aligned sensor ends for simultaneous assay of a sample. The transmission ends of the combined discrete fibers are addressed for interrogation to produce the fiber optic sensor.

Figure 2:
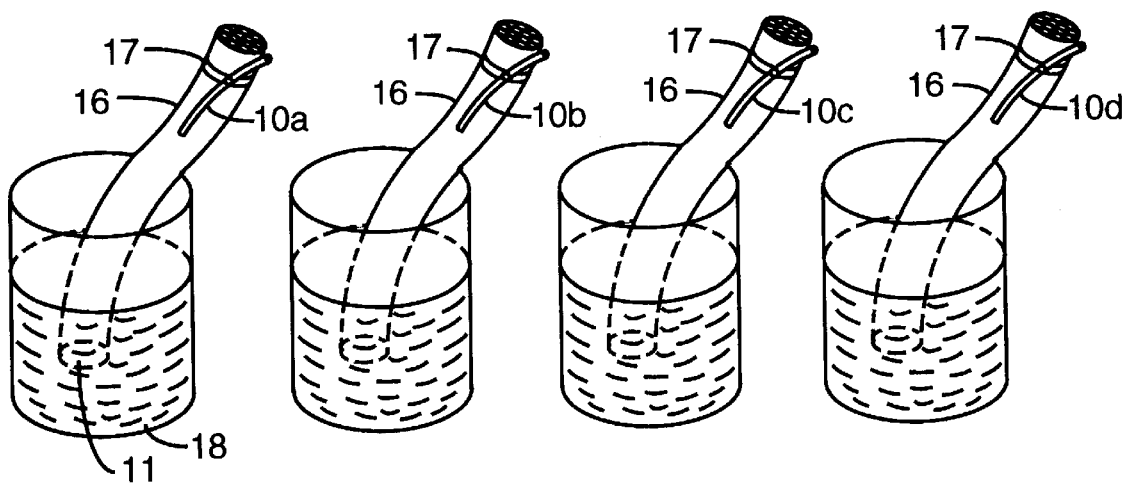
FIG. 2 illustrates a plurality of differing batches of treatment solution with the sensor ends of the group of fibers of FIG. 1 being immersed for treatment in one of the fiber batches.

FIG. 1, illustrates a particularly preferred embodiment that details one method of providing the optical fibers with attached biological binding partners. A plurality of optical fibers 10 are provided, each fiber having a sensor end 11 and a transmission end 12. The fibers are arranged together to form a plurality of fiber groups or bundles 16, as shown in FIG. 2, with the fibers in each bundle disposed coaxially alongside each other with the sensor ends 11 of each fiber commonly aligned at the same end of the bundle. The fibers comprising each bundle may be optionally marked 17 to permit their identification when subsequently removed from the bundle.

As shown in FIG. 2, each bundle of fibers is separately treated to attach a particular species of biological binding partner 18 to the sensor ends 11 of the optical fibers comprising the particular bundle. Many methods for immobilizing biological binding partners 18 on a variety of solid surfaces are known in the art. In general, the desired component may be covalently bound or noncovalently attached through nonspecific binding.

In preparing the sensor end 11 for attachment of the binding partner, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like.

If covalent bonding between a biological binding partner and the surface of the sensor end 11 is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like.

Covalent linkage of the binding partner to the sensor end may be direct or through a covalent linker. Generally linkers are either hetero- or homo-bifunctional molecules that contain two or more reactive sites that may each form a covalent bond with the respective binding partner. Linkers suitable for joining biological binding partners are well known to those of skill in the art. For example, biological binding partners may be joined by a peptide linker, by a straight or branched chain carbon chain linker, or by a heterocyclic carbon. Heterobifunctional cross linking reagents such as active esters of N-ethylmaleimide have been widely used. See, for example, Lerner et al. *Proc. Nat. Acad. Sci.* (USA), 78: 3403–3407 (1981) and Kitagawa et al. *J. Biochem.*, 79: 233–236 (1976), which are incorporated herein by reference.

The manner of linking a wide variety of compounds to various surfaces is well known and is amply illustrated in the literature. Proteins, for example, may be joined to linkers or to functional groups on the sensor end 11 by coupling through their amino or carboxyl termini, or through side groups of various constituent amino acids. Thus, coupling through a disulfide linkage to a cystein is common.

Similarly, methods for immobilizing nucleic acids by introduction of various functional groups to the molecules is known (see, e.g., Bischoff et al., *Anal. Biochem.* 164:336–344 (1987); Kremsky et al., *Nuc. Acids Res.* 15:2891–2910 (1987) which are incorporated herein by reference). Modified nucleotides can be placed on the target using PCR primers containing the modified nucleotide, or by enzymatic end labeling with modified nucleotides.

Figure 3:
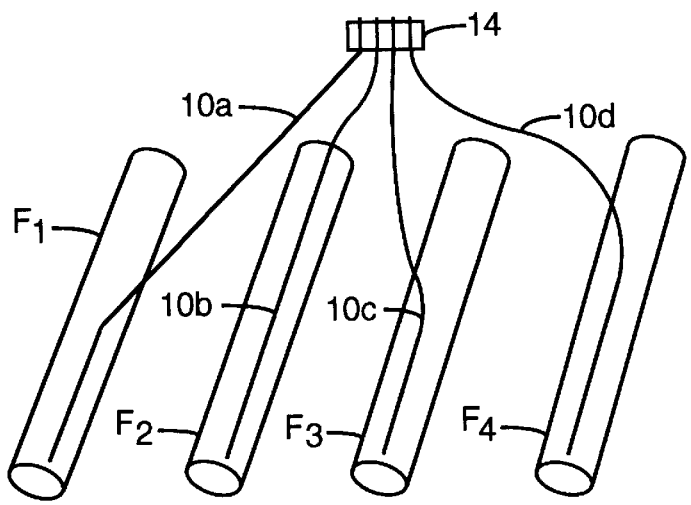
FIG. 3 illustrates differing groups of previously treated fibers lying side-by-side with fibers being singulated from each group for gathering into a common high density array.

Referring to FIG. 3, after the biological binding partners 18 are attached to the sensor faces 11 of the optical fibers 10 comprising each bundle, individual fibers, or groups of fibers, are separated from each bundle. In FIG. 3, only four fiber bundles $F_1$–$F_4$ are illustrated. In the process of being separated from each of the respective fiber bundles $F_1$–$F_4$ are individual fibers $10_a$–$10_d$. These respective fibers are being regrouped into optical fiber array 14.

The individual fibers or groups of fibers, may be marked prior to separation from the original bundle to facilitate identification of the binding partner bound to a particular fiber or group during later assembly steps. The separated fibers, or groups of fibers, are recombined with fibers or groups of fibers, separated from different bundles to form an optical fiber array 14 comprising a plurality of fibers or groups of fibers where each fiber or group of fibers bears a different species of biological binding partner.

FIG. 4 illustrates that members of the optical fiber array 14 are oriented such that the sensor ends 11 of all of the constituent optical fibers 10 are commonly aligned at the same end of the optical fiber array 14 thereby forming a sensor face 13. The fibers may be arranged in a substantially planar configuration or tiered, as illustrated in FIGS. 6A and 6B.

The fibers may be bundled at the sensor face 13 in a substantially random or haphazard manner with the relative location of a the sensor end 11 of a particular fiber within the sensor face 13 being determined by chance. Alternatively, the fibers may be positioned within the fiber array in a highly ordered manner such that the location of any particular optical fiber 10 in the sensor face 13 is predetermined.

The transmission ends 12 of the optical fibers comprising the optical fiber array 14 are addressed to permit interrogation and detection of binding events to the biological binding partners attached to the sensor face 13. Addressing is accomplished by any of a number of means well known to those of skill in the art. In a preferred embodiment, the transmission ends 12 of individual optical fibers, or groups of optical fibers all bearing the same species of biological binding partner, are spatially addressed. This comprises localizing the optical fibers or bundles of optical fibers at fixed locations relative to the other optical fibers or bundles of optical fibers comprising the optical fiber array 14, see e.g. FIG. 4. Most typically this may be accomplished by attaching the fiber array to a fiber optic connector and ferrule (e.g. see AMP, Inc. Harrisburg, Pa.).

Alternatively, the transmission ends 12, may be addressed by attaching the transmission end of each optical fiber 10 or bundle of optical fibers bearing a particular biological binding partner to an individual detector. Each detector is subsequently known to be associated with a particular biological binding partner and there is no need to preserve a fixed spatial relationship between any of the transmission ends 12.

Detection of a signal from the biosensor (optical array) may be accomplished by visual inspection of the transmission face 15 of the optical fiber array 14 or by the use of one or more detectors 20. As indicated above, the transmission face may be permanently or removably attached to a single optical lens or system of multiple optical lenses. The lens or lenses may be arranged to focus an optical signal from the entire transmission face 15 or from selected subregions of the transmission face. In a preferred embodiment, lenses will be arranged to each focus an optical signal from the portion of the transmission face 15 corresponding to a single biological binding partner. In the extreme case, the signal for each optical fiber comprising the optical fiber array 14 will be individually focused.

Again with a lens or lens system present, the signal may be simply detected visually. However, in a preferred embodiment, the use of detectors is contemplated. Preferred detectors are devices that convert an optical signal into a digital or analog electrical signal. Typically detectors are of two general types: phototubes and charge coupled devices (CCDs). A single photomultiplier or CCD element may be utilized to measure the aggregate signal provided by the entire transmission face 15 of the biosensor. More preferably, however, multiple CCD elements or phototubes are used to each detect a signal representing binding of a single species of biological binding partner present at the sensor face 13 of the optical fiber array 14.

The detector system may be employed with a computerized data acquisition system and analytical program. In this embodiment, providing a fully automated, computer controlled processing apparatus and measurement system, the data obtained from the biosensor is processed into immediately useful information. By using such fully automated, computerized apparatus and analytical systems, not only are a variety of different measurements made and diverse parameters measured concurrently within a single fluid sample, but also many different fluid samples may be analyzed individually seriatim for detection of multiple analytes of interest concurrently—each individual fluid sample following its predecessor in series.

II. Methods of Use

A variety of in vitro measurements and analytical determinations may be made using a fiber optic biosensor prepared in accordance with the present invention. In vitro applications and assay techniques may be performed concurrently using one or multiple fluid samples. Each concurrently conducted measurement or determination for different analytes of interest is made individually, accurately and precisely. The observed results are then correlated and/or computed to provide precise information regarding a variety of different parameters or ligands individually.

The fiber optic biosensor of the present invention may also be employed in a variety of different in vivo conditions with both humans and animals. The present invention provides accurate and precise measurements and determinations using a single discrete fiber optic biosensor rather than the conventional bundle of different sensors joined together for limited purposes. The present invention thus provides a minimum-sized diameter sensor for in vivo catheterization: a minimum intrusion into the bloodstream or tissues of the living subject for assay purposes, and a minimum of discomfort and pain to the living subject coupled with a maximum of accuracy and precision as well as a multiplicity of parameter measurement in both qualitative and/or quantitative terms.

The biosensor of the present invention may be utilized for the detection of a wide variety of analytes, depending on the particular biological binding partner selected. As indicated above, biological binding partners are molecules that specifically recognize and bind other molecules thereby forming a binding complex. Typical binding complexes include, but are not limited to, antibody-antigen, lectin-carbohydrate, nucleic acid-nucleic acid, biotin-avidin, receptor-receptor ligand, etc. Either member of the binding complex may be used as the biological binding member attached to the sensor end 11 of the optical fibers comprising the biosensor. Thus, for example, where it is desired to detect an antibody in a sample, the corresponding antigen may be attached to the sensor end. Conversely, where it is desired to detect the antigen in the sample, the antibody may be attached to the sensor end.

The selection of binding partners for a particular assay is well known to those of skill in the art. Typically, where proteins are to be detected, antibodies are most preferred as the biological binding partner. Where enzymatic substrates are to be detected, enzymes are preferred biological binding partners, and where nucleic acids are to be detected, nucleic acid binding partners are most preferred. Thus, for example, fiber optic biosensors have been described that utilize enzymes such as xanthine oxidase and peroxidase to detect hypoxanthine and xanthine (Hlavay et al., *Biosensors and Bioelectronics,* 9(3): 189–195 (1994), that use alkaline phosphatase to detect organophosphorous-based pesticides (Gao et al. *Proceedings—Lasers and Electro-Optics Society, Annula Meeting,* 8(4): abstract 20782 (1994), and that use antibodies or DNA binding proteins (Anderson, et al., *Fiber Optic Medical and Fluorescent Sensors and Applications, Proc. S.P.I.E.* 1648: 39–43 (1992).

Of course the biosensor may be designed to simultaneously detect several different classes of analyte. Thus the sensor may bear a combination of two or more different classes of biological binding partner. The sensor face 13 will bear one or more binding partners selected, for example, from the group consisting of nucleic acids, proteins, antibodies, carbohydrates, biotin, avidin, and lectins.

In the simplest application, the biosensor of the present invention may be utilized to detect a single analyte in a test sample. The test sample may be in vivo, in culture, or in vitro. The assay may register simple presence or absence of the analyte or may quantify the amount of analyte present in the sample.

The assay may be run in either a direct or a competitive format. In a direct format, the amount of analyte is determined directly measuring the analyte bound to the biological binding partner. In a competitive format, a known analyte is present in the sample and the test analyte is detected by its ability to compete the known analyte from the biological binding partners present on the sensor face 13.

In a preferred method of use, the optical fibers 10 comprising the optical fiber array 14 conduct an optical signal indicative of the binding between a biological binding partner on the sensor face 11 and the analyte in the sample. The optical signal may be produced by a number of means known to those of skill in the art. Typically the optical signal is generated by a fluorescent, luminescent, or colorimetric label present at the sensor end 11 of the optical fiber 10. Typically the concentration of label at the sensor end of the optical fiber is a function of the concentration of analyte that specifically binds to the biological binding partner present on that sensor end.

Methods of providing a label whose concentration is a function of the amount of an analyte specifically associated with a biological binding partner are well known to those of skill in the art. In the simplest approach, the analyte itself is labeled. Binding of the analyte to the binding partner then brings the label into proximity with the sensor end 11 to which the binding partner is attached. Alternatively, a labeled "blocking" analyte may be provided in the test sample or pre-bound to the biosensor. Displacement of the labeled "blocking" analyte by the unlabeled test analyte in the sample produces a reduction of label bound to the sensor end where the reduction is proportional to the concentration of unlabeled analyte in the test sample.

Other approaches may use a second biological binding partner that itself is labeled. The first biological binding partner attached to the sensor end binds and thereby immobilizes the analyte. The second, labelled binding partner then binds to the analyte immobilized on the sensor end thereby bringing the label in close proximity to the sensor end where it may be detected.

Luminescent labels are detected by measuring the light produced by the label and conducted along the optical fiber. Luminescent labels typically require no external illumination.

In contrast colorimetric or fluorescent labels typically require a light source. Colorimetric labels typically produce an increase in optical absorbance and/or a change in the absorption spectrum of the solution. Colorimetric labels are measured by comparing the change in absorption spectrum or total absorbance of light produced by a fixed light source. In the present invention, the change in light absorbance or absorption spectrum is preferably detected through the optical fibers comprising the biosensor. The change in absorbance, or absorption spectrum, may be measured as a change in illumination from an absolutely calibrated light source, or alternatively may be made relative to a second "reference light source". The light source may be external to the biosensor or may be provided as an integral component. In one embodiment, some of the constituent optical fibers will conduct light from the signal and/or reference source to the sensor face. For maximum sensitivity the light used to measure absorbance, or absorption spectrum, changes will be directed directly at the sensor face of the biosensor.

Fluorescent labels produce light in response to excitation by a light source. The emitted light, characteristically of a different (lower) wavelength than the excitation illumination, is detected through the optical fiber to which the fluorescent label has become bound.

The excitation illumination may be provided by an integral component of the biosensor or by a separate light source according to a number of methods well known to those of skill in the art. Evanescent wave systems involve introducing a light beam at the transmission end 12 of the optical fiber. This light beam is conducted along the fiber until it reaches the sensor end 11 of the fiber where it generates in the test solution an electromagnetic waveform known as the evanescent wave component. The evanescent wave component may be sufficient to excite a fluorophore and produce a fluorescent signal. (See, for example U.S. Pat. Nos. 4,447,546 and 4,909,990 which are incorporated herein by reference).

In another embodiment, the excitation illumination is provided external to the biosensor. It is particularly preferred that the illumination be provided as a "transillumination" normal to the sensor ends 11 of the optical fibers (see, e.g. FIG. 4). This provides an increased signal to noise ratio as, in this configuration, most of the excitation illumination will not be conducted along the optical fibers. The individual optical fibers 10 comprising the biosensor may be tiered, for example, as shown in FIGS. 6A and 6B, to prevent individual fibers from shadowing each other when transilluminated.

To optimize a given assay format one of skill can determine sensitivity of fluorescence detection for different combinations of optical fiber, sensor face configuration, fluorochrome, excitation and emission bands and the like. The sensitivity for detection of analyte by various optical fiber array configurations can be readily determined by, for example, using the biosensor to measure a dilution series of fluorescently labeled analytes. The sensitivity, linearity, and dynamic range achievable from the various combinations of fluorochrome and biosensor can thus be determined. Serial dilutions of pairs of fluorochromes in known relative proportions can also be analyzed to determine the accuracy with which fluorescence ratio measurements reflect actual fluorochrome ratios over the dynamic range permitted by the detectors and biosensor.

Use in Comparative Genomic Hybridization

In a particularly preferred embodiment, the biosensor of the present invention will be used in a Comparative Genomic Hybridization (CGH) assay. Comparative genomic hybridization (CGH) is a recent approach used to detect the presence and identify the chromosomal location of amplified or deleted nucleotide sequences. (See, Kallioniemi et al., *Science* 258: 818–821 (1992), WO 93/18186, and copending application U.S. Ser. No. 08/353,018, filed on Dec. 9, 1994, which are incorporated herein by reference).

In the traditional implementation of CGH, genomic DNA is isolated from normal reference cells, as well as from test cells (e.g., tumor cells). The two nucleic acids (DNA) are labelled with different labels and then hybridized in situ to metaphase chromosomes of a reference cell. The repetitive sequences in both the reference and test DNAs may be removed or their hybridization capacity may be reduced by some means such as an unlabeled blocking nucleic acid (e.g. Cot-1). Chromosomal regions in the test cells which are at increased or decreased copy number can be quickly identified by detecting regions where the ratio of signal from the two DNAs is altered. For example, those regions that have been decreased in copy number in the test cells will show relatively lower signal from the test DNA than the reference compared to other regions of the genome. Regions that have been increased in copy number in the test cells will show relatively higher signal from the test DNA.

In one embodiment, the present invention provides a CGH assay in which the biosensor of the present invention replaces the metaphase chromosome used as the hybridization target in traditional CGH. Instead, the biological binding partners present on the biosensor are nucleic acid sequences selected from different regions of the genome. The biosensor itself becomes a sort of "glass chromosome" where hybridization of a nucleic acid to a particular binding partner is informationally equivalent to hybridization of that nucleic acid to the region on a metaphase chromosome from which the biological binding partner is derived. In addition, nucleic acid binding partners not normally contained in the genome, for example virus nucleic acids, can be employed.

Figure 5:
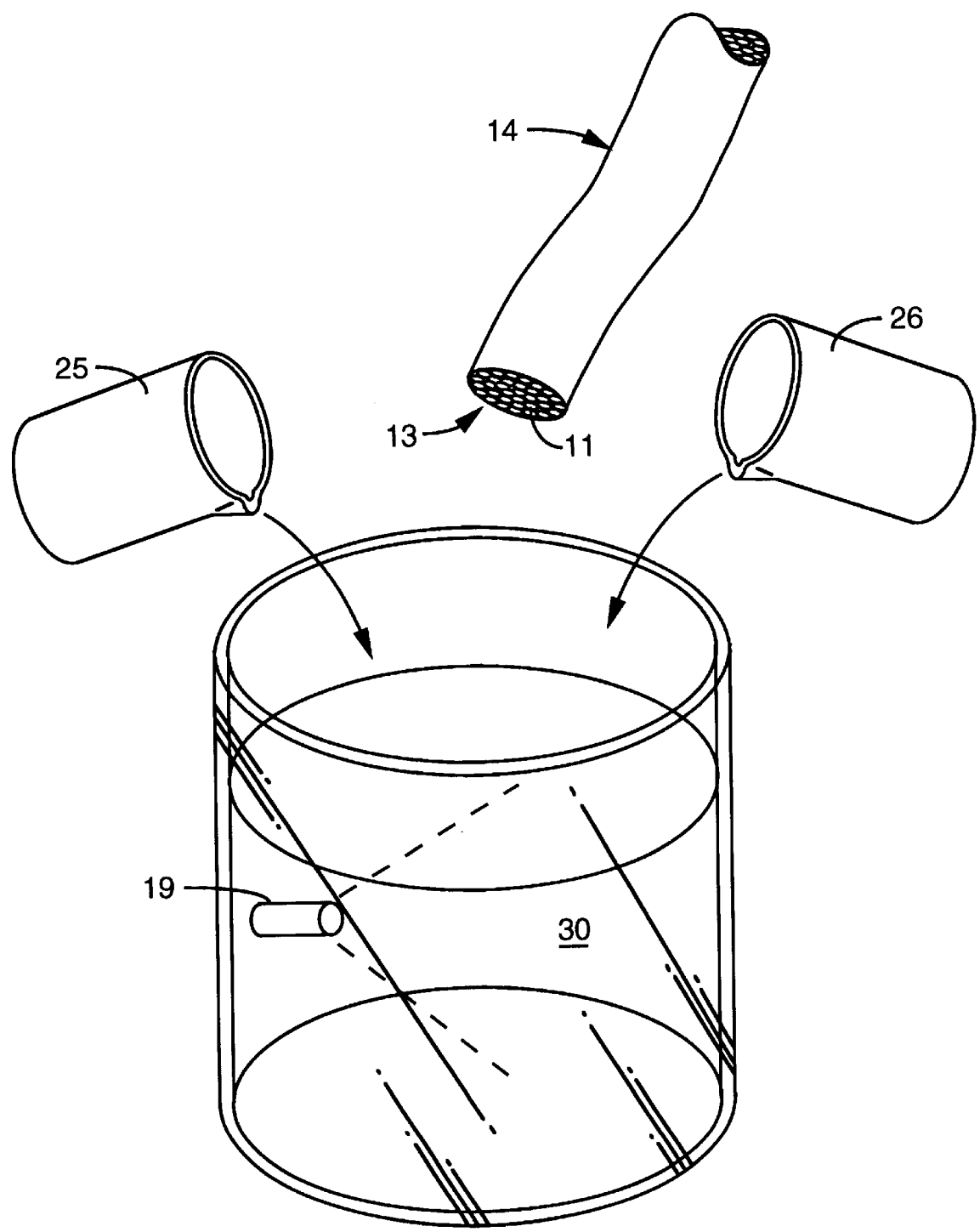
FIG. 5 illustrates a comparative genomic hybridization process being carried out with two samples for comparison having been previously tagged with differing fluorophores and being added together in a common batch.

More particularly, in a CGH assay, the biosensor may be utilized in methods for quantitatively comparing copy numbers of at least two nucleic acid sequences in a first collection of nucleic acid molecules relative to the copy numbers of those same sequences in a second collection, as illustrated in FIG. 5. The method comprises labeling the nucleic acid molecules in the first collection 25 and the nucleic acid molecules in the second collection 26 with first and second labels, respectively thereby forming at least two collections of nucleic acid probes. The first and second labels should be distinguishable from each other.

As used herein, the term "probe" is thus defined as a collection of nucleic acid molecules (either RNA or DNA) capable of binding to a target nucleic acid of complementary sequence through one or more types of chemical bonds, usually through hydrogen bond formation. The probes are preferably directly or indirectly labelled as described below. They are typically of high complexity, for instance, being prepared from total genomic DNA or mRNA isolated from a cell or cell population.

The probes 30 thus formed are contacted, either simultaneously or serially, to a plurality of target nucleic acids, present on the sensor face 13 of the biosensor of array 14 under conditions such that nucleic acid hybridization to the target nucleic acids can occur. Here a tranilluminating light source 19 is utilized. After contacting the probes to the target nucleic acids the amount of binding of each probe, and ratio of the binding of the probes is determined for each species of target nucleic acid. Typically the greater the ratio of the binding to a target nucleic acid, the greater the copy number ratio of sequences in the two probes that bind to nucleic acid. Thus comparison of the ratios of bound labels among target nucleic acid sequences permits comparison of copy number ratios of different sequences in the probes.

In a preferred embodiment, the sequence complexity of each target nucleic acid in the biosensor is much less than the sequence complexity of the first and second collections of labeled nucleic acids. The term "complexity"is used here according to standard meaning of this term as established by Britten et al. *Methods of Enzymol.* 29:363 (1974). See, also Cantor and Schimmel *Biophysical Chemistry: Part III* at 1228–1230 for further explanation of nucleic acid complexity.

The methods are typically carried out using techniques suitable for fluorescence in situ hybridization. Thus, the first and second labels are usually fluorescent labels.

To inhibit hybridization of repetitive sequences in the probes to the target nucleic acids, unlabeled blocking nucleic acids (e.g., Cot-1 DNA) can be mixed with the probes. Thus, the invention focuses on the analysis of the non-repetitive sequences in a genome. However, use of repetitive sequences as targets on teh biosensor and omiting the blocking nucleic acids would permit relative copy number determinations to be made for repetitive sequences.

In a typical embodiment, one collection of probe nucleic acids is prepared from a test cell, cell population, or tissue under study; and the second collection of probe nucleic acids is prepared from a reference cell, cell population, or tissue. Reference cells can be normal non-diseased cells, or they can be from a sample of diseased tissue that serves as a standard for other aspects of the disease. For example, if the reference probe is genomic DNA isolated from normal cells, then the copy number of each sequence in that probe relative to the others is known (e.g., two copies of each autosomal sequence, and one or two copies of each sex chromosomal sequence depending on gender). Comparison of this to a test probe permits detection in variations from normal. Alternatively the reference probe may be prepared from genomic DNA from a primary tumor which may contain substantial variations in copy number among its different sequences, and the test probe may prepared from genomic DNA of metastatic cells from that tumor, so that the comparison shows the differences between the primary tumor and its metastasis. Further, both probes may be prepared from normal cells. For example comparison of mRNA populations between normal cells of different tissues permits detection of differential gene expression that is a critical feature of tissue differentiation. Thus in general the terms test and reference are used for convenience to distinguish the two probes, but they do not imply other characteristics of the nucleic acids they contain.

Target nucleic acids

The target nucleic acids comprising the biological binding partners attached to the sensor ends 11 of the optical fibers 10 and the probes may be, for example, RNA, DNA, or cDNA. The nucleic acids may be derived from any organism. Usually the nucleic acid in the target sequences and the probes are from the same species.

The "target nucleic acids" comprising biological binding partners typically have their origin in a defined region of the genome (for example a clone or several contiguous clones from a genomic library), or correspond to a functional genetic unit, which may or may not be complete (for example a full or partial cDNA). The target nucleic acids can also comprise inter-Alu or Degenerate Oligonucleotide Primer PCR products derived from such clones. If gene expression is being analyzed, a target element can comprise a full or partial cDNA.

The target nucleic acids may, for example, contain specific genes or, be from a chromosomal region suspected of being present at increased or decreased copy number in cells of interest, e.g., tumor cells. The target nucleic acid may also be an mRNA, or cDNA derived from such mRNA, suspected of being transcribed at abnormal levels.

Alternatively, target nucleic acids may comprise nucleic acids of unknown significance or location. The array of such target nucleic acids comprising the sensor face 13 of a biosensor of the present invention could represent nucleic acids derived from locations that sample, either continuously or at discrete points, any desired portion of a genome, including, but not limited to, an entire genome, a single chromosome, or a portion of a chromosome. The number of target elements and the complexity of the nucleic acids in each would determine the density of sampling. For example an biosensor bearing 300 different species of target nucleic acid (biological binding partners), each target nucleic acid being DNA from a different genomic clone, could sample the entire human genome at 10 megabase intervals. An array of 30,000 elements, each containing 100 kb of genomic DNA could give complete coverage of the human genome.

Similarly, an array of target nucleic acids comprising nucleic acids from anonymous cDNA clones would permit identification of those that might be differentially expressed in some cells of interest, thereby focusing attention on study of these genes.

In some embodiments, previously mapped clones from a particular chromosomal region of interest are used as targets. Such clones are becoming available as a result of rapid progress of the worldwide initiative in genomics.

Mapped clones can be prepared from libraries constructed from single chromosomes, multiple chromosomes, or from a segment of a chromosome. Standard techniques are used to clone suitably sized fragments in vectors such as cosmids, yeast artificial chromosomes (YACs), bacterial artificial chromosomes (BACs) and P1 phage.

While it is possible to generate clone libraries, as described above, libraries spanning entire chromosomes are also available commercially. For instance, chromosome-specific libraries from the human and other genomes are available from Clonetech (South San Francisco, Calif.) or from The American Type Culture Collection (see, ATCC/ NIH Repository of Catalogue of Human and Mouse DNA Probes and Libraries, 7th ed. 1993).

If necessary, clones described above may be genetically or physically mapped. For instance, FISH and digital image analysis can be used to identify and map the locations on a chromosome to which specific cosmid inserts hybridize. This method is described, for instance, in Lichter et al., Science, 247:64–69 (1990). The physically mapped clones can then be used to more finally map a region of interest identified using CGH or other methods.

One of skill will recognize that each target nucleic acids may be selected so that a number of nucleic acids of different length and sequence represent a particular region on a chromosome. Thus, for example, a the sensor face 13 of the biosensor may bear more than one copy of a cloned piece of DNA, and each copy may be broken into fragments of different lengths. One of skill can adjust the length and complexity of the target sequences to provide optimum hybridization and signal production for a given hybridization procedure, and to provide the required resolution among different genes or genomic locations. Typically, the target sequences will have a complexity between about 1 kb and about 1 Mb.

Preparation of probe nucleic acids

As with target nucleic acids (those attached to the fiber optic sensor), a wide variety of nucleic acids can be used as probe nucleic acids in the methods of the present invention. The probes may be comprise, for example, genomic DNA representing the entire genome from a particular organism, tissue or cell type or may comprise a portion of the genome, such as a single chromosome.

To compare expression levels of a particular gene or genes, the probe nucleic acids can be derived from mRNA or cDNA prepared from an organism, tissue, or cell of interest. For instance, test cDNA or mRNA, along with mRNA or cDNA from normal reference cells, can be hybridized to an array of target nucleic acids on the sensor comprising clones from a normalized cDNA library. In addition, probes made from genomic DNA from two cell populations can be hybridized to a target cDNA array to detect those cDNAs that come from regions of variant DNA copy number in the genome.

The methods of the invention are suitable for comparing copy number of particular sequences in any combination of two or more populations of nucleic acids. One of skill will recognize that the particular populations of sample nucleic acids being compared is not critical to the invention. For instance, genomic or cDNA can be compared from two related species. Alternatively, levels of expression of particular genes in two or more tissue or cell types can be compared. As noted above, the methods are particularly useful in the diagnosis of disease.

Standard procedures can be used to isolate nucleic acids (either DNA or mRNA) from appropriate tissues (see, e.g., Sambrook, et al., Molecular Cloning—A Laboratory Manual, Cold Spring Harbor Laboratory, Cold Spring Harbor, N.Y. (1985)). Conventional methods for preparation of cDNA from mRNA can also be used.

The particular cells or tissue from which the nucleic acids are isolated will depend upon the particular application. Typically, for detection of abnormalities associated with cancer, genomic DNA is isolated from tumor cells. For prenatal detection of disease, fetal tissue will be used.

If the tissue sample is small, so that a small amount of nucleic acids is available, amplification techniques such as the polymerase chain reaction (PCR) using degenerate primers can be used. For a general description of PCR, see, PCR Protocols, Innis et al. eds. Academic Press, 1990. In addition, PCR can be used to selectively amplify sequences between high copy repetitive sequences. These methods use primers complementary to highly repetitive interspersed sequences (e.g., Alu) to selectively amplify sequences that are between two members of the Alu family (see, Nelson et al., Proc. Natl. Acad. Sci. USA 86:6686 (1989)).

CGH, at the cytogenetic level, facilitates the search for disease genes by identifying regions of differences in copy number between a normal and tumor genome, for example. For instance, CGH studies have been applied to the analysis of copy number variation in breast cancer (see, e.g., Kallioniemi et al. *Proc. Natl. Acad. Sci. USA* 91:2156–2160 (1994)).

In CGH, the resolution with which a copy number change can be mapped is on the order of several megabases. With the present invention the resolution is a function of the length of the genomic DNA segments comprising the target nucleic acid sequences and the difference in map position between neighboring clones. Resolution of more than a factor of 10 better than with standard CGH can be achieved with the present invention. This improved localization will facilitate efforts to identify the critical genes involved in a disease, and permit more sensitive detection of abnormalities involving a small region of the genome, such as in microdeletion syndromes.

Labeling nucleic acid probes

As noted above, the nucleic acids which are hybridized to the target nucleic acids are preferably labeled to allow detection of hybridization complexes. The nucleic acid probes used in the hybridization described below may be detectably labeled prior to the hybridization reaction. Alternatively, a detectable label may be selected which binds to the hybridization product. As noted above, the target nucleic acid array is hybridized to two or more probe nucleic acids, either simultaneously or serially. Thus, the probes are each preferably labeled with a separate and distinguishable label.

The particular label or detectable group attached to the probe nucleic acids is selected so as to not significantly interfere with the hybridization of the probe to the target sequence. The detectable group can be any material having a detectable physical or chemical property. Such detectable labels have been well-developed in the field of nucleic acid hybridizations and in general most any label useful in such methods can be applied to the present invention. Thus a label is any composition detectable by spectroscopic, photochemical, biochemical, immunochemical, electrical, optical or chemical means.

However, preferred labels produce an optical signal. Thus, particularly useful labels in the present invention include fluorescent dyes (e.g., fluorescein isothiocyanate, texas red, rhodamine, and the like) and labels that produce a colorimetric signal such as various enzymes (e.g., horse radish peroxidase, alkaline phosphatase and others commonly used in an ELISA).

The nucleic acids can be indirectly labeled using ligands for which detectable anti-ligands are available. For example, biotinylated nucleic acids can be detected using labeled avidin or streptavidin according to techniques well known in the art. In addition, antigenic or haptenic molecules can be detected using labeled antisera or monoclonal antibodies. For example, N-acetoxy-N-2-acetylaminofluorene-labelled or digoxigenin-labelled probes can be detected using antibodies specifically immunoreactive with these compounds (e.g., FITC-labeled sheep anti-digoxigenin antibody (Boehringer Mannheim)). In addition, labeled antibodies to thymidine-thymidine dimers can be used (Nakane et al. *ACTA Histochem. Cytochem.* 20:229 (1987)).

Generally, labels which are detectable in as low a copy number as possible, thereby maximizing the sensitivity of the assay, and yet be detectable above any background signal are preferred. A label is preferably chosen that provides a localized signal, thereby providing spatial resolution of the signal from each target element.

The labels may be coupled to the DNA in a variety of means known to those of skill in the art. In a preferred embodiment the probe will be labeled using nick translation or random primer extension (Rigby, et al. *J. Mol. Biol.,* 113: 237 (1977) or Sambrook, et al., *Molecular Cloning—A Laboratory Manual,* Cold Spring Harbor Laboratory, Cold Spring Harbor, N.Y. (1985)).

Hybridization of labeled nucleic acids to targets

The copy number of particular nucleic acid sequences in two probes are compared by hybridizing the probes to one or more target nucleic acid arrays (biosensors). The hybridization signal intensity, and the ratio of intensities, produced by the probes on each of the target elements is determined. Typically the greater the ratio of the signal intensities on a target nucleic acid the greater the copy number ratio of sequences in the two probes that bind to that target sequence. Thus comparison of the signal intensity ratios among target elements permits comparison of copy number ratios of different sequences in the probes.

Standard hybridization techniques are used to probe a target nucleic acid array. Suitable methods are described in references describing CGH techniques (Kallioniemi et al., *Science* 258: 818–821 (1992) and WO 93/18186). Several guides to general techniques are available, e.g., Tijssen, *Hybridization with Nucleic Acid Probes,* Parts I and II (Elsevier, Amsterdam 1993). For a description of techniques suitable for in situ hybridizations see, Gall et al. *Meth. Enzymol.,* 21:470–480 (1981) and Angerer et al. in *Genetic Engineering: Principles and Methods* Setlow and Hollaender, Eds. Vol 7, pgs 43–65 (plenum Press, New York 1985).

Generally, nucleic acid hybridizations utilizing the biosensors of the present invention comprise the following major steps: (1) prehybridization treatment to increase accessibility of target DNA, and to reduce nonspecific binding; (2) hybridization of the mixture of nucleic acids to the nucleic acid targets on the biosensor; (3) posthybridization washes to remove nucleic acid fragments not bound in the hybridization and (4) detection of the hybridized nucleic acid fragments. The reagent used in each of these steps and their conditions for use vary depending on the particular application.

In some applications it is necessary to block the hybridization capacity of repetitive sequences. A number of methods for removing and/or disabling the hybridization capacity of repetitive sequences are known (see, e.g., WO 93/18186).

For instance, bulk procedures can be used. In many genomes, including the human genome, a major portion of shared repetitive DNA is contained within a few families of highly repeated sequences such as Alu. These methods exploit the fact that hybridization rate of complementary sequences increases as their concentration increases. Thus, repetitive sequences, which are generally present at high concentration will become double stranded more rapidly than others following denaturation and incubation under hybridization conditions. The double stranded nucleic acids are then removed and the remainder used in hybridizations. Methods of separating single from double stranded sequences include using hydroxyapatite or immobilized complementary nucleic acids attached to a solid support. Alternatively, the partially hybridized mixture can be used and the double stranded sequences will be unable to hybridize to the target.

Alternatively, unlabeled sequences which are complementary to the sequences whose hybridization capacity is to be inhibited can be added to the hybridization mixture. This method can be used to inhibit hybridization of repetitive sequences as well as other sequences. For instance, "Cot-1" DNA can be used to selectively inhibit hybridization of repetitive sequences in a sample. To prepare Cot-1 DNA, DNA is extracted, sheared, denatured and renatured to a $C_0t\sim1$ (for description of reassociation kinetics and $C_0t$ values, see, Tijssen, supra at pp 48–54). Because highly repetitive sequences reanneal more quickly, the resulting hybrids are highly enriched for these sequences. The remaining single stranded (i.e., single copy sequences) is digested with S1 nuclease and the double stranded Cot-1 DNA is purified and used to block hybridization of repetitive sequences in a sample. Although Cot-1 DNA can be prepared as described above, it is also commercially available (BRL). Reassociation to large $C_0t$ values will result in blocking DNA containing reptitive sequences that are present at lower copy number.

Analysis of Detectable Signals from Hybridizations

Standard methods for detection and analysis of signals generated by labeled probes can be used. In particular, the optical signal produced by binding of a labeled probe to a particular binding partner will be carried along the optical fibers 10, to which that binding partner is attached. As indicated above, the optical signal may be visualized directly or transduced into an analog or digital electronic signal by means of a detector 20. To facilitate the display of results and to improve the sensitivity of detecting small differences in fluorescence intensity, a detector and a digital signal analysis system is preferably used. The detector may be equipped with one or more filters to pass the emission wavelengths while filtering out excitation wavelengths thereby increasgn the signal to noise ratio. The use of filters will also facilitate distinguishing between binding events involving the two, or more, differently labeled probes. Such detector/filter/signal processing systems are well known to those of skill in the art.

What is claimed is:

1. A detector for detecting signal light from an array of light sources, said detector comprising a multiplicity of simple lenses joined together to form a compound lens; and a detection device, wherein each simple lens is positioned such that each light source of said array of light sources is located at the focal point of a single simple lens of said compound lens, and wherein signal light from a light source of the said array of light sources passes through a simple lens of said compound lens and is then detected by said detection device.

2. The detector of claim 1, wherein the detection device comprises a photomultiplier element.

3. The detector of claim 1, wherein the detection device comprises a charge coupled device element.

4. The detector of claim 1, further comprising a beam splitter positioned to direct an excitation light through each simple lens of said compound lens to each light source of said array of light sources.

5. The detector of claim 4, further comprising an excitation light source to provide said excitation light.

6. The detector of claim 1, further comprising a second lens, wherein signal light from a light source of said array of light sources passes through said second lens after passing through a simple lens of said compound lens.

7. The detector of claim 6, further comprising an optical filter, wherein said signal light passes through said optical filter after passing through said second lens.

* * * * *